US006146839A

United States Patent [19]

Morikawa et al.

[11] Patent Number: 6,146,839

[45] **Date of Patent: *Nov. 14, 2000**

[54] ***CHLAMYDIA PNEUMONIAE* ANTIGENS, METHOD FOR PRODUCTION OF THE ANTIGENS, METHOD AND REAGENTS FOR MEASUREMENT OF ANTI-*CHLAMYDIA PNEUMONIAE* ANTIBODIES USING THE ANTIGENS**

[75] Inventors: Toshihide Morikawa; Kiyotaka Kawagoe; Hiroshi Izutsu; Akifumi Iguchi; Mitsuo Yamaki, all of Ibaraki, Japan

[73] Assignee: Hitachi Chemical Company, Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/930,775

[22] PCT Filed: Mar. 28, 1996

[86] PCT No.: PCT/JP96/00827

§ 371 Date: Sep. 29, 1997

§ 102(e) Date: Sep. 29, 1997

[87] PCT Pub. No.: WO96/30763

PCT Pub. Date: Oct. 3, 1996

[30] Foreign Application Priority Data

Mar. 28, 1995 [JP] Japan .................................... 7-069436

[51] Int. Cl.[7] .......................... G01N 33/571; C12Q 1/00; A61K 39/118; A61K 35/14

[52] U.S. Cl. .......................... 435/7.36; 424/263.1; 435/4; 435/7.1; 530/384

[58] Field of Search .............................. 424/263.1; 435/4, 435/7.1, 7.36; 530/384

[56] References Cited

FOREIGN PATENT DOCUMENTS

| | | |
|---|---|---|
| 0363106 | 4/1990 | European Pat. Off. . |
| 0456524 | 11/1991 | European Pat. Off. . |

OTHER PUBLICATIONS

Iljima et al "Characterization of *Chlamydia pneumoniae* species–specific proteins immunodominant in humans". J. Clin. Microbiol., vol. 32, No. 3, pp. 583–588, Mar. 1, 1994.

Campbell et al., "Serological Response to *Chlamydia Pneumoniae* Infection", *J. of Clin. Microbio.*, 28(6):1261–1264, 1990.

*Primary Examiner*—Rodney P. Swartz

*Attorney, Agent, or Firm*—Pennie & Edmonds LLP

[57] ABSTRACT

The present invention relates to a *Chlamydia pneumoniae* antigen comprising protein derived from the outer membrane of *Chlamydia pneumoniae,* a method for producing a *Chlamydia pneumoniae* antigen which comprises solubilizing the cytosol and the cytoplasmic membrane of *Chlamydia pneumoniae* elementary body with an ionic detergent, and then removing the solubilized portion to obtain the residue, a method for measuring an anti-*Chlamydia pneumoniae* antibody which comprises using the *Chlamydia pneumoniae* antigen, and a reagent for measuring anti-*Chlamydia pneumoniae* antibody, said reagent comprising the *Chlamydia pneumoniae* antigen.

In accordance with the present invention, there are provided a *Chlamydia pneumoniae* antigen which has a high species-specificity, very few clinically problematic false negatives, and few false positives, a method for producing said antigen, a method for measuring an anti-*Chlamydia pneumoniae* antibody, and a reagent for measuring an anti-*Chlamydia pneumoniae* antibody.

14 Claims, 2 Drawing Sheets

*CHLAMYDIA PNEUMONIAE* ANTIGENS, METHOD FOR PRODUCTION OF THE ANTIGENS, METHOD AND REAGENTS FOR MEASUREMENT OF ANTI-*CHLAMYDIA PNEUMONIAE* ANTIBODIES USING THE ANTIGENS

FIELD OF THE INVENTION

The present invention relates to *Chlamydia pneumoniae* antigens useful for diagnosis of *Chlamydia pneumoniae* infections, methods for production of the antigens, methods and reagents for measurement of anti-*Chlamydia pneumoniae* antibodies using the antigens.

BACKGROUND ART

Chlamydia are obligate intracellular parasites that are capable of surviving only in a host cell. Its growth cycle is unique, and the elementary body (hereinafter referred to as EB) of Chlamydia that is morphologically outside of the cell is taken up into the cell to form a vacuole inclusion body, which is then converted to a reticulate body (hereinafter referred to as RB). RB owns a propagating capability but lacks an infecting capability and the RB that has propagated in the cell is soon converted to an EB, which by breaking the inclusion body and disrupting the cell wall, comes out of the cell. EB lacks a propagating capability but owns an infecting capability. Currently there are confirmed four kinds of Chlamydia species (*C. trachomatis, C. psittaci, C. pneumoniae,* and *C. pecorum*), among which *Chlamydia pneumoniae* is known to infect humans via air infection.

In recent years, *Chlamydia pneumoniae* has attracted widespread attention as the causative microorganism of respiratory infections such as pneumonia, bronchitis, acute upper airway inflammation and the like. According to the serological epidemiological study conducted in various parts of the world, the prevalence of the antibody against *Chlamydia pneumoniae* is 40 to 50% in Europe and the USA, 60% or greater in Taiwan, Panama, Iran and the like, and 50 to 60% in Japan. As the actual situations on *Chlamydia pneumoniae* infections become more apparent, interests in the infections are mounting.

The most sensitive serological method for diagnosis of Chlamydia infections is the indirect microimmunofluorescence test (micro-IF test) by Wang and Grayston (Trachoma and related disorders caused by Chlamydial agents, Excerpta Medica, Amsterdam, pp.273–288, 1971). However, since the test procedure of the micro-IF test is complicated, it has not been employed as a diagnostic method in the clinical laboratories. Furthermore, the standard micro-IF test requires the purified EB of Chlamydia. The micro-IF test also requires the morphological and structural integrity of the microorganism to be identified in order to carry out the immunological fluorescent reactions. Hence the morphologically or structurally altered EB or the disrupted EB cannot be used. However, since EB has an infectious capability and toxicity, the use of an intact EB as the antigen material requires a special facility which has been rendered infection-defense. Therefore, the EB treated with a fixing agent such as formaldehyde, acetone and the like is usually used as the antigen.

On the other hand, the recently developed enzyme-linked immunosorbent assay (ELISA) has an advantage that it can process a large number of samples in a simple and rapid manner. There are reports on the methods for measurement of anti-Chlamydia antibody using the ELISA, and most of the methods employ the intact EB of Chlamydia as the antigen material. Therefore, the presence of non-specific reactions is known which result from the use of an inadequately purified antigen. This is caused largely by the complex antigenicity of Chlamydia. As the antigenicity of Chlamydia, it has been believed, there are the genus-specific antigens, the species-specific antigens, and the biobar-specific antigens.

As a representative genus-specific antigen of Chlamydia, there is known lipopolysaccharide (hereinafter referred to as LPS), which has a common antigen shared by the Re mutant LPS derived from some enterobacteria.

Furthermore, as a representative species-specific or biobar-specific antigen, there is known the Major Outer Membrane Protein of Chlamydia (hereinafter referred to as MOMP), which is considered to occupy approximately 60% of the outer membrane proteins of Chlamydia. However, the presence of the genus-specific antigenicity is also known for MOMP (Collett et al., Annu. Meet. Am. Soc. Microbiol., Washington, D.C., Abstract No. D-159, 1986).

The outer membrane antigens of Chlamydia other than MOMP are mainly genus-specific antigens, but in some the species-specific antigenicity is also present. For example, Iijima et al. report, based on the results of the immunoblot assay using the EB of *Chlamydia pneumoniae,* that the MOMP having a molecular weight (MW) of 40K daltons of *Chlamydia pneumoniae* is genus-specific, and the MW 43K-dalton, 46K-dalton and the 53K-dalton proteins are species-specific, and furthermore the MW 98K dalton-proteins are probably species-specific (Y. Iijima et al., Journal of Clinical Microbiology, p.583–588 (1994)).

As hereinabove described, the antigenicity of Chlamydia is very complicated and so antigens which are common to a genus Chlamydia exhibit a significantly different antigenicity among the different species. Hence, although the methods for measuring anti-*Chlamydia trachomatis* antibody are known (Japanese Unexamined Patent Publication No. Hei 4-297871), the methods cannot be simply used for measuring *Chlamydia pneumoniae* in a species-specific manner since the antigenicities of *Chlamydia pneumoniae* and *Chlamydia trachomatis* are quite different from each other. Also, anti-Chlamydia antibodies carried by individuals infected with *Chlamydia pneumoniae* show a diversity corresponding to the complex antigenicity of Chlamydia. Although the pattern varies with infected individuals, the use of EB itself as the antigen may cause non-specific reactions and hence a specific and highly precise measurement using it is difficult.

DISCLOSURE OF THE INVENTION

The first object of the present invention is to provide a *Chlamydia pneumoniae* antigen which has a high species-specificity, few clinically problematic false negatives, low false positives, and excellent reproducibility.

A second object of the present invention is to provide a method for producing a *Chlamydia pneumoniae* antigen which has a high species-specificity, few clinically problematic false negatives, and low false positives.

A third object of the present invention is to provide a method for measuring anti-*Chlamydia pneumoniae* antibodies, which provides a high species-specificity, very few clinically problematic false negatives, and few false positives, permits simple measurement and simple collection of specimens, reflects the clinical picture of the specimen donor, and is highly sensitive.

A fourth object of the present invention is to provide reagents for measuring ant-*Chlamydia pneumoniae* antibodies which provides a high species-specificity, very few clinically problematic false negatives and few false positives, permits simple measurement, and is highly sensitive.

The subject matters of the invention are as follows:

(1) A *Chlamydia pneumoniae* antigen comprising protein derived from the outer membrane of *Chlamydia pneumoniae.*

(2) The *Chlamydia pneumoniae* antigen of the above (1) which does not cause substantially non-specific reactions with anti-*Chlamydia trachomatis* antibodies or with anti-*Chlamydia psittaci* antibodies.

(3) The *Chlamydia pneumoniae* antigen of the above (1) or (2) wherein the protein derived from the outer membrane of *Chlamydia pneumoniae* contains at least one of the three proteins having a molecular weight of about 43K daltons, about 46K daltons, and about 53K daltons.

(4) The *Chlamydia pneumoniae* antigen of one of the above (1) to (3) wherein the protein derived from the outer membrane of *Chlamydia pneumoniae* contains the three proteins having a molecular weight of about 43K daltons, about 46K daltons, and about 53K daltons.

(5) A method for producing a *Chlamydia pneumoniae* antigen which comprises solubilizing the cytosol and the cytoplasmic membrane of a *Chlamydia pneumoniae* elementary body with an ionic detergent, and then removing the solubilized portion to obtain the residue portion.

(6) A method for measuring an anti-*Chlamydia pneumoniae* antibody which comprises using a *Chlamydia pneumoniae* antigen of any of the above (1) to (4).

(7) The method of the above (6) for measuring an anti-*Chlamydia pneumoniae* antibody, which comprises immobilizing the *Chlamydia pneumoniae* antigen of one of the above (1) to (4) to a solid carrier, bringing said carrier into contact with a specimen to be measured, bringing the resulting antigen-antibody complex into contact with a labeled antibody against the antibody in the specimen, measuring the amount of the label on the bound or unbound labeled antibody, and determining the anti-*Chlamydia pneumoniae* antibody in the specimen from the measured value.

(8) The method of the above (7) for measuring an anti-*Chlamydia pneumoniae* antibody, wherein specimens to be measured are human tears, human throat swabs, or human sera.

(9) The method of the above (7) or (8) for measuring an anti-*Chlamydia pneumoniae* antibody, wherein the labeled antibody is a labeled anti-human IgG antibody, a labeled anti-human IgA antibody or a labeled anti-human IgM antibody.

(10) The method of any of the above (7) to (9) for measuring an anti-*Chlamydia pneumoniae* antibody, wherein the labeled antibody is an enzyme labeled antibody.

(11) A reagent for measuring an anti-*Chlamydia pneumoniae* antibody, which comprises the *Chlamydia pneumoniae* antigen of any of the above (1) to (4).

(12) The reagent of the above (11) for measuring an anti-*Chlamydia pneumoniae* antibody, said reagent comprising an immobilized antigen immobilized on a solid carrier and a labeled antibody which reacts with the antibody to be measured.

(13) The reagent of the above (12) for measuring an anti-*Chlamydia pneumoniae* antibody, wherein the solid carrier is polystyrene beads or a polystyrene microtiter plate.

(14) The reagent of the above (12) or (13) for measuring an anti-*Chlamydia pneumoniae* antibody, wherein the labeled antibody is an enzyme-labeled antibody.

(15) The reagent of the above (14) for measuring an anti-*Chlamydia pneumoniae* antibody, wherein the enzyme-labeled antibody is an alkaline phosphatase-labeled antibody or a horse radish peroxidase-labeled antibody.

The present invention is explained in detail below.

The outer membrane of *Chlamydia pneumoniae* is the cell wall of *Chlamydia pneumoniae* devoid of the cytoplasm and the cytoplasmic membrane thereof and is composed mainly of proteins and lipids.

The *Chlamydia pneumoniae* antigen of the present invention comprises proteins derived from the above-mentioned outer membrane of *Chlamydia pneumoniae.*

Among the *Chlamydia pneumoniae* antigens, those which do not produce substantially non-specific reactions with *Chlamydia trachomatis* or *Chlamydia psittaci* are preferred since they have very few clinically problematic false negatives or false positives. As used herein, the phrase "do not produce substantially non-specific reactions" means that there are no or almost no non-specific reactions.

As the proteins derived from the outer membrane of *Chlamydia pneumoniae,* for example, there are the proteins having a molecular weight of about 30K daltons, about 37K daltons, about 40K daltons, about 43K daltons, about 46K daltons, about 53K daltons, about 60K daltons, and about 98K daltons.

As the *Chlamydia pneumoniae* antigens of the present invention, those antigens containing at least one of the three proteins of about 43K daltons, about 46K daltons, and about 53K daltons in molecular weight which are species-specific to *Chlamydia pneumoniae* are preferred among the proteins derived from the above-mentioned outer membrane of *Chlamydia pneumoniae.*

As the *Chlamydia pneumoniae* antigens of the present invention, those antigens containing the three proteins of the about 43K daltons, about 46K daltons, and about 53K daltons in molecular weight are more preferred among the proteins derived from the above-mentioned outer membrane of *Chlamydia pneumoniae,* since they have an excellent ability of dealing with the diversity of the anti-Chlamydia antibodies carried by individuals infected with *Chlamydia pneumoniae.*

Furthermore, as the *Chlamydia pneumoniae* antigens of the present invention, those antigens containing a protein of about 98K daltons in molecular weight in addition to at least one of the three proteins of about 43K daltons, about 46K daltons, and about 53K daltons in molecular weight are preferred among the proteins derived from the above-mentioned outer membrane of *Chlamydia pneumoniae,* since they have a more excellent ability of dealing with the above-mentioned diversity.

Now the method for producing the *Chlamydia pneumoniae* antigen of the present invention is explained below.

The *Chlamydia pneumoniae* antigen of the present invention can be obtained from the cell mass of *Chlamydia pneumoniae,* and preferably EB out of the *Chlamydia pneumoniae* cell mass is used as the raw material since it can provide antigens having a favorable characteristics.

As a method for obtaining the *Chlamydia pneumoniae* antigen of the present invention from *Chlamydia pneumoniae* EB, there is described, for example, a method wherein the cytoplasm and the cytoplasmic membrane of *Chlamydia pneumoniae* EB are solubilized using an ionic detergent and then the solubilized portion is removed to obtain the residue portion. The method is preferable since it permits easy production of the antigen and the antigen obtained shows a favorable antigenicity. As the above-mentioned ionic detergent, the anion sarcosine detergent is preferred since the antigen obtained shows a favorable antigenicity and Sarcosyl (sarcosinate N-lauroyl sodium) is especially preferred. Furthermore, when the cytoplasm and the cytoplasmic membrane of *Chlamydia pneumoniae* EB is solubilized with an ionic detergent it is preferred that a nuclease such as deoxyribonuclease (DNase) and ribonuclease (RNase) is reacted to solubilize and remove nucleic acids.

The residue portion obtained by solubilizing the cytoplasm and the cytoplasmic membrane of *Chlamydia pneumoniae* EB with an ionic detergent followed by removing the solubilized portion is composed mainly of the cell wall of *Chlamydia pneumoniae* EB devoid of the cytoplasm and the cytoplasmic membrane, i.e. the outer membrane of *Chlamydia pneumoniae.* The outer membrane of *Chlamydia pneumoniae* contains the above-mentioned proteins having a molecular weight of about 30K daltons, about 37K daltons, about 40K daltons, about 43K daltons, about 46K daltons, about 53K daltons, about 60K daltons, and about 98K daltons and traces of other proteins.

As the *Chlamydia pneumoniae* antigen of the present invention, part of this outer membrane of *Chlamydia pneumoniae,* i.e. Chlamydia outer membrane complex (hereinafter referred to as COMC) can be used.

Furthermore, as the *Chlamydia pneumoniae* antigen of the present invention, the reaction product obtained by reacting the residue portion with a solubilizing agent. As such a solubilizing agent, there is mentioned, for example, sodium dodecyl sulfate (SDS). The reaction product thus obtained contains the solubilized products or the decomposed products of the above-mentioned residue portion.

These *Chlamydia pneumoniae* antigens have a high species-specificity and very few clinically problematic false-negatives and few false-positives.

Among these *Chlamydia pneumoniae* antigens, the above-mentioned residue component itself which is mainly composed of the *Chlamydia pneumoniae* outer membrane is preferably used since it excels in the above effects and in reproducibility.

The method for measuring the anti-*Chlamydia pneumoniae* antibody of the present invention is not limited as long as the above-mentioned *Chlamydia pneumoniae* antigen is used as part or all of the antigen.

As a method for measuring the antibody, there are mentioned as preferred methods, for example, the sandwich type enzymeimmunoassay that employs various labeled antibodies, the latex agglutination method that employs latex carrier particles, the immunoturbidometric assay, and the like.

The sandwich type immunoassay is described in detail below.

As a method for measuring anti-*Chlamydia pneumoniae* antibodies by means of the sandwich type immunoassay using the *Chlamydia pneumoniae* antigen of the present invention, a method can be used wherein the above antigen is physically or chemically immobilized on the solid carrier to prepare the immobilized antigen, said immobilized antigen is brought into contact with the specimen to incubate for a certain period of time thereby causing the anti-*Chlamydia pneumoniae* antibody, when present in said specimen, to bind to said immobilized antigen to form an antigen-antibody complex on the solid carrier, which is washed as desired, and then the labeled antibody against the antibody in the specimen is contacted wherein the specimen and the labeled antibody are optionally brought into contact with each other simultaneously.

When the above-mentioned antigen-antibody complex has been formed, it is further bound to the labeled antibody so as to be immobilized on the solid carrier. Subsequently the amount of the label on the labeled antibody which is bound or unbound on the solid carrier is determined by a method depending on the kind of the label, and from the determined value the presence or the amount of the anti-*Chlamydia pneumoniae* antibody in the specimen can be obtained.

As the solid carrier, for example, there can be used plastic materials such as polystyrene, vinyl chloride, etc., filamentous materials such as nitrocellulose, nylon, etc., inorganic materials such as glass, silica gel, etc., which may be in any form including a titerplate, beads, magnetic beads, a paper disk, threads, etc. Polystyrene beads or a polystyrene microtiter plate are preferred since they are easy to handle and the polystyrene microtiter plate is most preferred since it is especially easy to handle.

Furthermore, as the method for immobilizing the antigen on the above-mentioned solid carrier, there are used methods based on physical adsorption, the covalent bonding method employing $BrCN_2$ etc.

As the specimen there are mentioned, for example, various fluid components of the humans, and human tears, human throat swabs, or human sera are preferred since they reflect the clinical picture of the specimen donor, and generally the human sera are used.

As the labeled antibody, there are mentioned the labeled antibody against the antibody (for example, human antibody) in the specimen which has been labeled with various labels. As the antibodies to be labeled, there are mentioned an anti-human IgG antibody, an anti-human IgA antibody, an anti-human IgM antibody, or partially decomposed products thereof such as F(ab')2, Fab etc., and the like, which are used as appropriate according to the kind of the antibody to be measured.

It has been believed that after the surface infection of *Chlamydia pneumoniae,* the IgM antibody appears in 1 to 2 weeks, and the IgG antibody also appears relatively early and disappears with time but persists for a long period of time. On the other hand, it has been believed that the secretary type IgA antibody is playing a role in cellular immunity and in protecting against reinfection.

Therefore, in the step of contacting the labeled antibody against the antibody in the above-mentioned specimen, it is preferred that the labeled antibodies obtained by labeling different kinds of antibodies are separately reacted for measurement. As the labeled antibodies obtained by labeling different kinds of antibodies, there are mentioned a labeled anti-IgG antibody, a labeled anti-IgA antibody, a labeled anti-IgM antibody, and the like.

As the labels used for the labeled antibody, there can be used, for example, enzymes, radioisotopes, fluorescent compounds, chemiluminescent compounds, and the like, and in consideration of sensitivity, safety, simplicity, etc., enzymes are preferably used. As the enzymes, there are mentioned, for example, malate dehydrogenase (enzyme number 1.1.1.37), glucose-6-phosphate dehydrogenase (enzyme number 1.1.1.49), glucose oxidase (enzyme number 1.1.3.4), horse radish peroxidase (enzyme number 1.11.1.7), acetylcholine esterase (enzyme number 3.1.1.7), alkaline phosphatase (enzyme number 3.1.3.1), glucoamylase (enzyme number 3.2.1.3), lysozyme (enzyme number 3.2.1.17), β-galactosidase (enzyme number 3.2.1.23), and the like.

As the enzyme labeled antibodies, preferably the alkaline phosphatase-labeled antibodies or the horse radish peroxidase-labeled antibodies are employed since they permit simple and sensitive assays, and these enzyme labeled antibodies are commercially available.

As is evident from the examples described below, the method for measuring the anti-*Chlamydia pneumoniae* antibody of the present invention has a good correlation with the results obtained by the indirect micro-IF test which employs the conventional Chlamydia EB, has a high species-specificity, and has very few clinically problematic false-negatives and few false-positives.

The reagent for measuring the anti-*Chlamydia pneumoniae* antibody of the present invention is not limited as long as the above-mentioned *Chlamydia pneumoniae* antigen is used as part or all of the antigen.

As the reagent for measuring the anti-*Chlamydia pneumoniae* antibody used in the above sandwich immunoassay, though the composing elements are different depending on the measuring method, there is mentioned, for example, a reagent which separately contains the immobilized antigen immobilized on the solid carrier and the labeled antibody reacting with the antibody to be measured.

As the solid carriers and labeled antibodies, there are those mentioned above.

The labeled antibody may be kept suspended in a buffer solution and the like.

As the reagent of the present invention, it is preferred that a labeled anti-human IgG antibody, a labeled anti-human IgA antibody, and a labeled anti-human IgM antibody are separately prepared as the labeled antibody for one specimen because it can reflect the clinical picture of the specimen donor.

In the reagent of the present invention, other components may be combined as desired. In the case of a reagent used in the sandwich immunoassay, for example, other components include a negative control sample, a positive control sample, a washing solution, and a standard material, and, in the case where the label is an enzyme, a reaction substrate, a dilution solution, a reaction stopping solution, and the like, which may be used alone or in combination. The reagent is very useful for diagnosis of *Chlamydia pneumoniae* infection.

As described above, the *Chlamydia pneumoniae* antigen of the present invention comprises proteins derived from the *Chlamydia pneumoniae* outer membrane, which proteins usually contain relatively or quite large amounts of *Chlamydia pneumoniae*-non-specific components. In accordance with the present invention, however, the anti-*Chlamydia pneumoniae* antibody can be quantitatively determined even by using such a *Chlamydia pneumoniae* antigen.

From this, the *Chlamydia pneumoniae* antigen of the present invention is considered to cause no substantially non-specific reactions between an anti-*Chlamydia trachomatis* antibody and an anti-*Chlamydia psittaci* antibody, and to have a high species-specificity, and thereby to have very few clinically problematic false negatives, and few false positives.

BEST MODE FOR CARRYING OUT THE INVENTION

Figure 1:
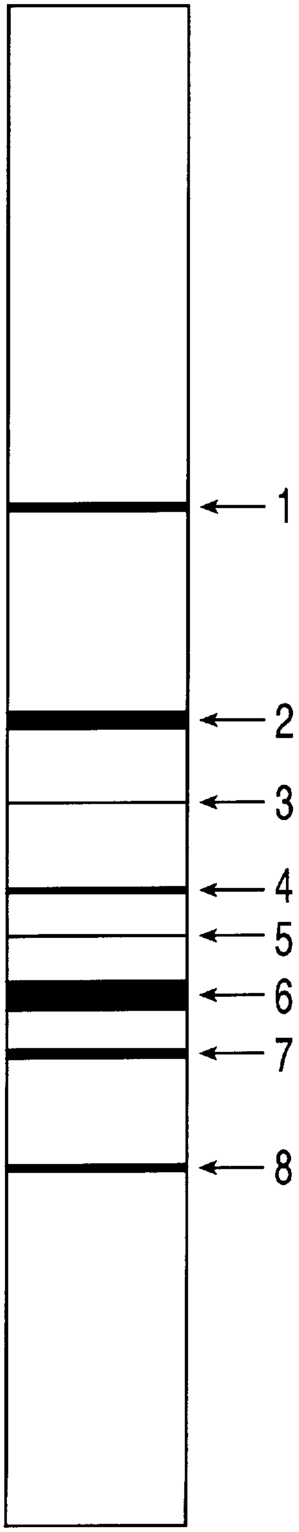
FIG. 1 shows a pattern of the SDS-polyacrylamide gel electrophoresis of the Sarcosyl-insoluble outer membrane fraction of *Chlamydia pneumoniae,* in which each arrow represents a protein having a molecular weight of: 1: about 98K daltons, 2: about 60K daltons, 3: about 53K daltons, 4: about 46K daltons, 5: about 43K daltons, 6: about 40K daltons, 7: about 37K daltons, and 8: about 30K daltons.

The present invention is now explained with reference to the following examples.

EXAMPLE

A) Purification of *Chlamydia pneumoniae* EB

As the Chlamydia, *Chlamydia pneumoniae* strain YK41 (Kanamoto et al., KANSENSHOUGAKU ZASSI (Journal of Infectious Diseases) 66(5), 637–641 (1992)) was used.

To the HL cells which had previously been infected with the YK41 strain and cultured for 4 days (in a polystyrene tissue culture 6-well plate) was added the SPG solution (an aqueous solution of sucrose 75.0 g, monopotassium phosphate 0.52 g, dipotassium phosphate 1.22 g, and glutamic acid 0.72 g dissolved in 1 liter of water, pH 7.4 to 7.6) at an amount of 1 ml/well. Using a silicone rubber block the HL cells were scraped off and the SPG solution containing the HL cells was collected.

The collected solution was diluted 48-fold in the SPG solution and then placed in a polystyrene centrifuge tube, which was then sonicated at one second interval for 30 times. The centrifuge tube was centrifuged at 1,500×g for three minutes, and the supernatant was collected to make the YK41 strain suspension ($10^5$ IFU/ml).

On the other hand, after 4 ml of about $8\times10^4$ cells/rnl suspension of the HL cells which had been grown in the MEM medium supplemented with 10% (v/v) fetal bovine serum (FBS) was dispensed into a 6-well culture plate, it was cultured at 36° C. in a 5% (v/v) $CO_2$ incubator for 3 days in order to prepare the monolayer of the cells. To this, 2 ml of the above suspension of the YK41 strain ($10^5$ IFU/ml) was inoculated and was subjected to centrifugation absorption (900×g, 60 min). After the adsorption, the inoculated solution was aspirated off, 4 ml of the Eagle MEM medium supplemented with 10% (v/v) FBS containing cycloheximide (1 $\mu$l/ml) was added thereto, and it was further cultured at 36° C. in the 5% (v/v) $CO_2$ incubator for 4 days. Then the infected cells were scraped off using a silicone rubber block to collect the suspension of the infected cells. At this time a cover slip of 13 mmin diameter was placed in the 6-well culture plate and was removed immediately before scraping off the infected cells. The cover slip was stained using the Cultureset™ (Ortho Diagnostic Systems Inc., Raritan, N.J., U.S.A.) to confirm the infection ratio.

After the cells in the above suspension of the infected culture were disrupted in the homogenizer, they were centrifuged at 20° C. for 10 minutes to collect the supernatant. Two parts of this supernatant were layered on two parts of 0.033 M Tris-HCl buffer, pH 7.2, containing 30% Urografin (diatrizoate meglumine and trizatesodium) (w/v) which had been layered on one part of 0.033 M Tris-HCl buffer, pH 7.2, containing 50% (w/v) sucrose, which were then centrifuged at 43,000×g, 20° C., for 60 minutes. The pellet thus obtained provided the crude purified EB.

One part of the suspension of the above crude purified EB was layered on three parts of 0.033 M Tris-HCl buffer, pH 7.2, having a gradient of 35 to 50 (w/v) Urografin, which was then centrifuged at 43,000×g, 20° C., for 60 minutes. The turbid layer in the middle phase after the centrifuge was collected to give the purified EB.

B) Acquisition of the sarcosine-insoluble outer membrane fraction of Chlamydia

The purified EB thus obtained was suspended into 0.01 M sodium phosphate buffer containing 2% (w/v) Sarcosyl, 1.5 mM EDTA (ethylenediaminetetraacetic acid) and 0.14 M saline (Sarcosyl buffer) (pH 8.0) and then was sonicated at 20 kHz for 60 seconds. After incubating at 37° C. for one hour, it was centrifuged at 100,000×g, 20° C., for 60 minutes. After the centrifugation, the pellet was suspended again in a small amount of the above Sarcosyl buffer and was centrifuged at 100,000×g, 20° C., for 60 minutes. After the centrifugation, the supernatant was collected again as the soluble fraction. The pellet was washed twice with PBS (pH 8.0) in order to remove the excess Sarcosyl. Subsequently, the above pellet was suspended in 0.02 M sodium phosphate buffer, pH 8.0, containing 10 mM $MgCl_2$ wherein DNase and RNase were each dissolved at 2.5 μg/ml, was reacted at 37° C. for 2 hours, and then was centrifuged at 100,000×g, 4° C., for 60 minutes. In order to remove the DNase and RNase which may remain in the residue, the residue was washed twice in PBS (pH 8.0) to obtain the residue component (Sarcosyl-insoluble outer membrane fraction of Chlamydia).

The residue component thus obtained was subjected to SDS-polyacrylamide gel electrophoresis to determine the molecular weight of each protein contained in the residue component.

The SDS-polyacrylamide gel electrophoresis was carried out according to the method described in Laemuli, (U.K. Nature, 227, 680–685, 1970), in a 4 to 20% (w/v) gradient of acrylamide gel. The electrophoresis buffer used was 0.025 M Tris buffer containing 1% (w/w) SDS and 0.2 M glycine. Ten μl per well of the sample to be electrophoresed was used which had previously been prepared by adding to 60 μl of the residue component (protein concentration 500 μg/ml) 60 μl of the sample treatment solution (0.125 M Tris buffer, pH 6.8, containing 4% (w/v) SDS, 2% (v/v) glycerol, 0.01% (w/v) BPB) and 12 μl of 2-mercaptoethanol as a reducing agent followed by treatment at 95° C. for 5 minutes. The electrophoresis was conducted at 40 mA for about 1 hour. As the molecular weight marker Kaleidoscope Prestain Standard (trade name of a BioRad product) was used and subjected the same electrophoretic condition as mentioned above to determine the molecular weight of proteins in each sample from their mobility.

Staining was conducted by the silver staining method using the Silver Staining Kit Wako (trade name, manufactured by Wako Pure Chemicals Industries, Ltd.).

FIG. 1 shows a pattern of the SDS-polyacrylamide gel electrophoresis. In FIG. 1 each arrow represents a protein having a molecular weight of: 1: about 98K daltons, 2: about 60K daltons, 3: about 53K daltons, 4: about 46K daltons, 5: about 43K daltons, 6: about 40K daltons, 7: about 37K daltons, and 8: about 30K daltons.

C) Measurement of an anti-*Chlamydia pneumoniae* antibody

The residue component obtained above, using as the antigen, was adjusted to a protein concentration of 5 μg/ml in the buffer for immobilizing the carrier (1 liter contains 2.93 g of $NaHCO_3$ and 1.59 g of $Na_2CO_3$) and its aliquot of 100 μl was dispensed into each well of a 96-well polystyrene microtiter plate, and then the plate was incubated at 4° C. overnight. It was then washed 3 times in 300 μl of PBS, pH 7.2, containing 0.05% (v/v) Tween 20 (hereinafter referred to as 0.05% (v/v) Tween 20-PBS) to remove the unadsorbed antigen. Then 250 μl of the blocking buffer containing 5% (w/v) bovine serum albumin (BSA) (manufactured by KPL) (the buffer for blocking and sample dilution) was added to each well and was incubated at 37° C. for 1 hour to prepare the antigen-immobilized plate. The plate was washed twice in 250 μl of 0.05% (v/v) Tween 20-PBS. Then after 100 μl of serum sample diluted in the buffer for blocking and sample dilution was added to the above antigen-immobilized plate it was incubated at 37° C. for 1 hour and washed 3 times in 250 μl of 0.05% (v/v) Tween 20-PBS. Then the anti-human IgG antibody labeled with alkaline phosphatase (the labeled antibody) was diluted to 1 μg/ml in 0.05% (v/v) Tween 20-PBS, 100 μl of which was dispensed into each well. After incubating at 37° C. for one hour, it was washed 3 times with 250 μl of 0.05% (v/v) Tween 20-PBS. Then 100 μl of a solution of p-NPP (p-nitrophenyl phosphate), a substrate of alkaline phosphatase, in diethanolamine (the substrate for enzyme reaction, concentration 1 mg/ml) was added to each well and incubated at room temperature for 10 minutes. The reaction was then stopped by adding 25 μl of 3N NaOH solution (the reaction stop solution) and the absorbance (405 nm) was determined by the microtiter plate reader (manufactured by Corona Denki K.K., trade name MTP-120 type).

D) Sensitivity and specificity to the human serum

This was specified by the indirect micro-IF test carried out as a control test. Sensitivity and specificity tests were carried out using 55 serum samples of *Chlamydia pneumoniae* antibody-positive individuals and 66 serum samples of *Chlamydia pneumoniae* antibody-negative individuals. The human serum was diluted 200-fold using 0.05% (v/v) Tween 20-PBS to prepare a specimen for measurement of the Chlamydia antibody. The indirect micro-IF test will be explained later.

In order to further clarify the effect of the present invention, measurement was conducted in the same method as the present invention except that the purified EB of *Chlamydia pneumoniae* strain YK41 was used as the antigen for measuring *Chlamydia pneumoniae* antibody to compare its sensitivity and specificity with those of the *Chlamydia pneumoniae* antigen of the present invention. The results are shown in Table 1 and FIG. 2.

Figure 2:
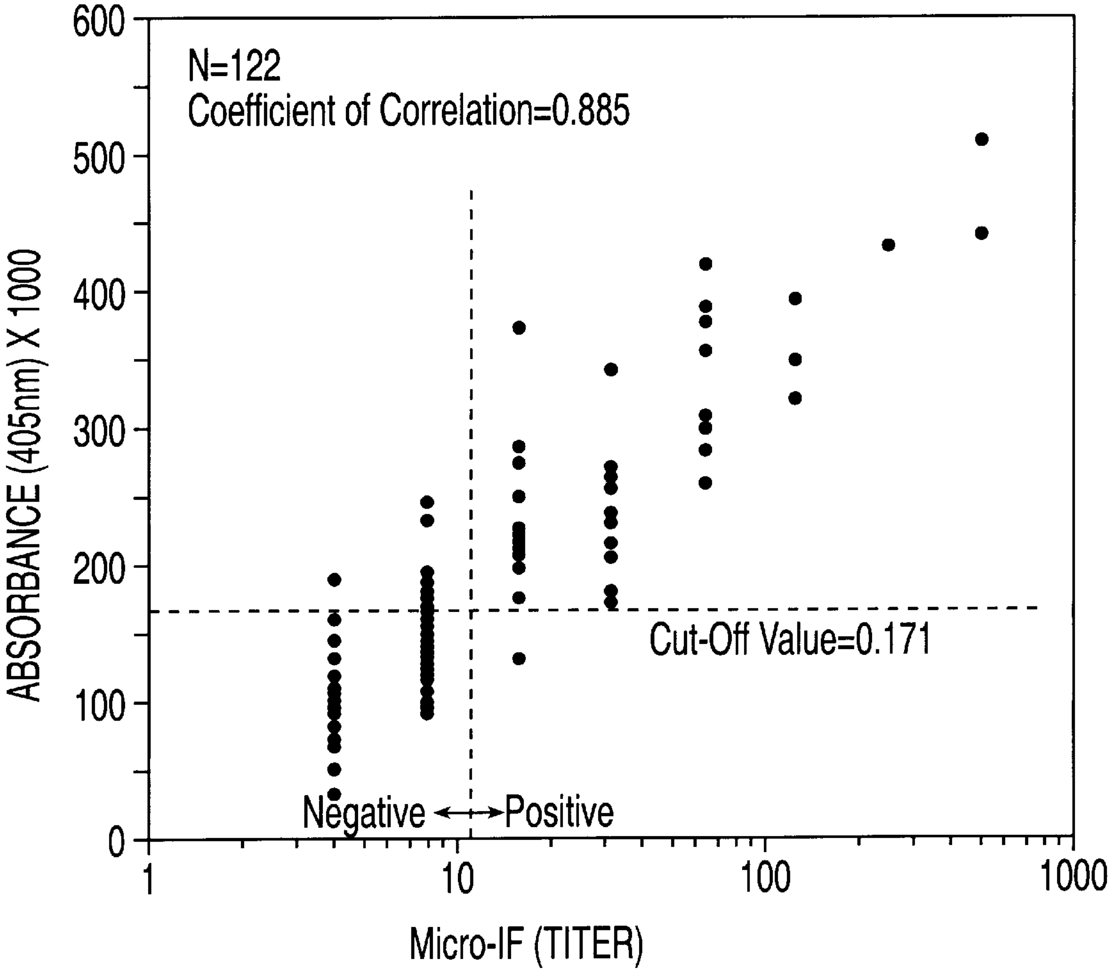
FIG. 2 is a graph showing correlation between an enzyme-linked immunosorbent assay (ELISA) using the *Chlamydia pneumoniae* antigen of the present invention and a micro-IF test using *Chlamydia pneumoniae* EB, in which the ordinate represents the absorbance at 405 nm of ELISA, and the abscissa represents the serum dilution factor (titer) of the micro-IF test.

FIG. 2 is a graph which compares a correlation of the enzyme-linked immunosorbent assay (ELISA) using the *Chlamydia pneumoniae* antigen of the present invention with the micro-IF test, wherein the ordinate represents the absorbance at 405 nm of ELISA and the abscissa represents the serum dilution factor (titer) of the micro-IF test.

TABLE 1

| Antigen used | Predictive Value of Positive Test (Sensitivity) (Positive samples = 55) | Predictive Value of Negative Test (Specificity) (Negative samples = 66) | Cut-Off Value |
|---|---|---|---|
| *C. pneumoniae* outer membrane complex | 98.2% (54) | 86.4% (57) | 0.171 |
| Purified elementary body (EB) | 54.5% (30) | 83.3% (55) | 0.453 |

The cut-off value of each test was defined as the mean of absorbances of 66 negative human sera plus the standard deviation.

The results in FIG. 2 show that the results obtained by the method of the present invention exhibit a very good correlation with those of the conventional micro-IF test.

The results in Table 1 also show that the *Chlamydia pneumoniae* antigen of the present invention has a more excellent coincidence with the mirco-IF test than the purified EB tested as the control antigen. In particular, it shows that it has no clinically problematic false negatives and thereby a high clinical usefulness.

E) Investigation on cross reactivity with the *Chlamydia trachomatis* antibody and with the *Chlamydia psittaci* antibody.

Reactivity with *Chlamydia pneumoniae, Chlamydia trachomatis*, and *Chlamydia psittaci* was tested using the indirect micro-IF test. The test was carried out as shown below in accordance with the method described in "Chlamydia Kansenshouno Kisoto Rinsho" (Basics and Clinical Pathology of Chlamydia Infections), pp. 62 to 91 (published by Kinbara Shuppan K.K. on Feb. 20, 1988).

Using *Chlamydia pneumoniae* strain TW-183, *Chlamydia trachomatis* strain L2, and *Chlamydia psittaci* strain Budgerigar-1, EB was obtained as in the above (A). The obtained EB was each mixed with 3% Normal Yolk Sac and was dotted in close proximity to each other on a slide glass. The dotted three kinds of EB were made into one group, and a total of 16 groups with four groups in a column and four groups of EB in a row were dotted on a slide glass. After dotting, acetone was added to the slide glass to fix EBs.

The human serum samples were diluted in a serial 2-fold dilution such as 2-, 4-, and 8-fold in 0.05% (v/v) Tween 20-PBS to prepare the sample solutions. The sample solutions were each added to the EB of the above groups, incubated at 37° C. for 30 minutes, the sample solutions were removed, and the slide glass was washed in Tween 20-PBS.

Anti-human IgG-FITC conjugate (a fluorescent antibody manufactured by Sigma Chemical Co. Ltd.) was added to EB of each of the above groups, incubated at 37° C. for 30 minutes, the sample solutions were removed, and then the slide glass was washed in Tween 20-PBS. The slide glass thus obtained was observed under a fluorescent microscope to examine the presence of fluorescence, and the highest dilution factor at which fluorescence was observed was defined as the titer with a result that titer 16 was set as the cut-off value.

From the results of the indirect micro-IF test, the samples were grouped into those having the *Chlamydia pneumoniae* antibody, those having the *Chlamydia trachomatis* antibody, and those having the *Chlamydia psittaci* antibody, which are shown in Table 2 to 4.

For the human serum samples tested by the above indirect micro-IF test (the sample solutions prepared in the same manner as for the above sample solution for measurement of said Chlamydia antibody), the antibody was detected in the method of the present invention as described in C). which are shown in Table 2 to 4.

The results revealed that the measurement method of the present invention has no cross reactivity with *Chlamydia trachomatis* or *Chlamydia psittaci.*

TABLE 2

| Sample | Micro-IF test (Titer) | | | The measuring method of the present invention |
|---|---|---|---|---|
| No. | *C. pneumoniae* | *C. psittaci* | *C. trachomatis* | (Absorbance) |
| A 1 | 64 | less than 8 | less than 8 | 0.372 |
| 2 | 32 | less than 8 | less than 8 | 0.172 |
| 3 | 32 | 8 | 8 | 0.301 |
| 4 | 16 | less than 8 | less than 8 | 0.207 |
| 5 | 64 | less than 8 | less than 8 | 0.277 |
| 6 | 16 | less than 8 | less than 8 | 0.270 |
| 7 | 32 | less than 8 | less than 8 | 0.234 |
| 8 | 512 | 8 | 16 | 0.501 |
| 9 | 128 | less than 8 | less than 8 | 0.387 |
| 10 | 512 | less than 8 | less than 8 | 0.434 |

TABLE 3

| Sample | Micro-IF test (Titer) | | | The measuring method of the present invention |
|---|---|---|---|---|
| No. | *C. pneumoniae* | *C. psittaci* | *C. trachomatis* | (Absorbance) |
| B 11 | less than 8 | less than 8 | 16 | 0.143 |
| 12 | less than 8 | less than 8 | 8 | 0.115 |
| 13 | less than 8 | less than 8 | 16 | 0.106 |
| 14 | less than 8 | less than 8 | 16 | 0.070 |
| 15 | 8 | less than 8 | 16 | 0.148 |
| 16 | less than 8 | less than 8 | 16 | 0.088 |
| 17 | 8 | 8 | 16 | 0.089 |
| 18 | less than 8 | less than 8 | 64 | 0.121 |
| 19 | less than 8 | less than 8 | 64 | 0.124 |
| 20 | less than 8 | 16 | 16 | 0.117 |

TABLE 4

| Sample | Micro-IF test (Titer) | | | The measuring method of the present invention |
|---|---|---|---|---|
| No. | *C. pneumoniae* | *C. psittaci* | *C. trachomatis* | (Absorbance) |
| B 21 | less than 8 | less than 8 | 128 | 0.117 |
| 22 | less than 8 | less than 8 | 128 | 0.120 |
| 23 | less than 8 | less than 8 | 64 | 0.063 |
| C 24 | less than 8 | 16 | 8 | 0.131 |
| 25 | less than 8 | 16 | less than 8 | 0.065 |

Table 2 to 4, A is a sample having the antibody to *C. pneumoniae,* B is a sample having the antibody to *C. trachomatis*, and C is a sample having the antibody to *C. psittaci* (the results by the micro-IF test).

The cut-off value in the example of the present invention was 0.171.

Industrial Applicability

The *Chlamydia pneumoniae* antigen of the present invention has a high species-specificity, very few clinically problematic false negatives, few false positives, and excellent reproducibility, and is therefore very useful for measuring the anti-*Chlamydia pneumoniae* antibody.

According to the method for producing the *Chlamydia pneumoniae* antigen of the present invention, it is possible to provide method for producing the antigen which has a high species-specificity, very few clinically problematic false negatives, and few false positives.

The method for measuring the anti-*Chlamydia pneumoniae* antibody of the present invention has a high species-specificity, very few clinically problematic false negatives, few false positives, permits simple measurement and simple collection of specimens, reflects the clinical picture of the specimen donor, and is highly sensitive, thereby making it very useful for diagnosis of *Chlamydia pneumoniae* infections.

The reagent for measuring the anti-*Chlamydia pneumoniae* antibody of the present invention has a high species-specificity, very few clinically problematic false negatives, few false positives, and is easy to measure, and is highly sensitive, and therefore valuable for diagnosis of *Chlamydia pneumoniae* infections.

What is claimed is:

1. A *Chlamydia pneumoniae* antigen which does not cause crossreactions with anti-*Chlamydia trachomatis* antibodies or with anti-*Chlamydia psittaci* antibodies, consisting essentially of a protein derived from the outer membrane of *Chlamydia pneumoniae,* said antigen being obtained by solubilizing the cytosol and the cytoplasmic membrane of a *Chlamydia pneumoniae* elementary body with an ionic detergent and then removing the solubilized portion to obtain the residue portion containing said antigen.

2. The *Chlamydia pneumoniae* antigen of claim 1, wherein the protein derived from the outer membrane of *Chlamydia pneumoniae* contains at least one of three proteins having molecular weights of about 43K daltons, about 46K daltons, and about 53K daltons, respectively.

3. The *Chlamydia pneumoniae* antigen of claim 1, wherein the protein derived from the outer membrane of *Chlamydia pneumoniae* contains three proteins having molecular weights of about 43K daltons, about 46K daltons, and about 53K daltons, respectively.

4. A method for producing a *Chlamydia pneumoniae* antigen which does not cause cross-reactions with anti-*Chlamydia trachomatis* antibodies or with anti-*Chlamydia psittaci* antibodies, comprising solubilizing the cytosol and the cytoplasmic membrane of a *Chlamydia pneumoniae* elementary body with an ionic detergent, and then removing the solubilized portion to obtain the residue portion containing said antigen.

5. A method for measuring an anti-*Chlamydia pneumoniae* antibody, which comprises using the *Chlamydia pneumoniae* antigen of claim 1.

6. The method of claim 5 for measuring an anti-*Chlamydia pneumoniae* antibody, which comprises immobilizing the *Chlamydia pneumoniae* antigen of claim 1 on a solid carrier, bringing said carrier into contact with a specimen to be measured, bringing the resulting antigen-antibody complex into contact with a labeled antibody against the antibody in the specimen, measuring the amount of the label on the bound or unbound labeled antibody, and determining the anti-*Chlamydia pneumoniae* antibody in the specimen from the measured value.

7. The method of claim 6 for measuring an anti-*Chlamydia pneumoniae* antibody, wherein the specimen to be measured includes human tears, a human throat swab, and human serum.

8. The method of claim 6 for measuring an anti-*Chlamydia pneumoniae* antibody, wherein the labeled antibody is a labeled anti-human IgG antibody, a labeled anti-human IgA antibody or a labeled anti-human IgM antibody.

9. The method of claim 6 for measuring an anti-*Chlamydia pneumoniae* antibody, wherein the labeled antibody is an enzyme labeled antibody.

10. A reagent for measuring an anti-*Chlamydia pneumoniae* antibody, which comprises the *Chlamydia pneumoniae* antigen of any of claim 1.

11. The reagent of claim 10 for measuring an anti-*Chlamydia pneumoniae* antibody, said reagent comprising the antigen immobilized on a solid carrier and a labeled antibody which reacts with the antibody to be measured.

12. The reagent of claim 11 for measuring an anti-*Chlamydia pneumoniae* antibody, wherein the solid carrier is polystyrene beads or a polystyrene microtiter plate.

13. The reagent of claim 11 for measuring an anti-*Chlamydia pneumoniae* antibody, wherein the labeled antibody is an enzyme-labeled antibody.

14. The reagent of claim 13 for measuring an anti-*Chlamydia pneumoniae* antibody, wherein the enzyme-labeled antibody is an alkaline phosphatase-labeled antibody or a horseradish peroxidase-labeled antibody.

* * * * *